United States Patent [19]

French et al.

[11] 4,023,398
[45] May 17, 1977

[54] APPARATUS FOR ANALYZING TRACE COMPONENTS

[76] Inventors: John Barry French, 4 Thornbank Road; Neil M. Reid, 165 Royal Orchard Blvd., both of Thornhill, Ontario; Janette A. Buckley, 6 Tepee Court, Willowdale, Ontario, all of Canada

[22] Filed: Mar. 3, 1975

[21] Appl. No.: 555,202

[52] U.S. Cl. .................. 73/23; 55/11; 55/102; 55/135; 55/269; 55/270; 62/55.5; 98/36; 250/281; 250/288

[51] Int. Cl.² ................. G01N 31/00

[58] Field of Search ........... 55/2, 111, 102, 135, 55/270, 269; 250/281, 288; 98/36; 62/55.5; 73/23

[56] References Cited
UNITED STATES PATENTS

| | | | |
|---|---|---|---|
| 3,008,543 | 11/1961 | Bourdale et al. | 55/334 |
| 3,119,243 | 1/1964 | Hnilicka et al. | 62/55.5 |
| 3,154,682 | 10/1964 | Hartz | 55/2 |
| 3,495,379 | 2/1970 | Hall et al. | 55/2 |
| 3,706,138 | 12/1972 | Schulerer | 98/36 |
| 3,920,987 | 11/1975 | Anbar et al. | 250/281 |

*Primary Examiner*—Bernard Nozick

*Attorney, Agent, or Firm*—Rogers, Bereskin & Parr

[57] ABSTRACT

Apparatus for analyzing sample gas consisting of a trace gas contained in a carrier gas. The sample gas is carried through a cylindrical duct; ions from the trace gas are formed, and are subjected to a transverse electric field which concentrates the flux of desired ions into an axial stream located away from the duct walls. The electric field may be produced by a combination of the duct walls and a central axial needle electrode in the duct, or by conical focussing screens or by cylindrical lens elements. The concentrated flux of ions passes through spaced interface and orifice plates containing a gas curtain between them and then passes into a vacuum chamber containing a mass spectrometer or other detector. The curtain gas, which blocks flow of carrier gas into the vacuum chamber, is cryo pumpable (e.g. $CO_2$). The vacuum chamber contains surfaces cooled so as to cause deposit of the curtain gas thereon, thereby maintaining a vacuum. The cryo pumpable curtain gas arrangement may also be used to transfer other species or materials, such as materials arranged in a continuous strip, between two gaseous media, one at lower pressure than the other, without transfer of one such medium into the other.

13 Claims, 22 Drawing Figures

APPARATUS FOR ANALYZING TRACE COMPONENTS

This invention relates to methods and apparatus for concentrating ions. The invention may be used for detecting and identifying trace gases contained in air or other carrier gas. Certain aspects of the invention also have a more general application, namely that of transferring species such as X-rays, photons or the like, or materials in a continuous strip, between a first gaseous medium and a second lower pressure gaseous medium, without significant transfer of one medium into the other. The invention will be described primarily with reference to the detection and analysis of trace gases by an analyzer such as a mass spectrometer. In the following description the term "sample gas" will be used as meaning the trace gas to be detected together with the carrier gas in which it is contained.

In prior art apparatus for detecting and analyzing trace gases contained in large quantities of air or other carrier gases, problems in achieving extreme sensitivity exist for a number of reasons, including the following.

Normally the mass spectrometer or other detector used must be located in a vacuum chamber, while the sample gas must be supplied from outside the vacuum chamber. In order to preserve the vacuum, the orifice through which the gaseous components are admitted into the vacuum chamber must be very small. In some cases pressure staging has been used to permit a larger orifice, but due to practical limitations on pump sizes the gain in orifice size has been relatively minor. The small orifice limits signal transmission into the vacuum chamber and hence limits the sensitivity of the device.

In addition, in the detection and analysis of trace gases the sample gas under investigation is usually ionized by electron impact normally to form sample gas ions. In atmospheric pressure chemical ionization systems, it is only after the sample gas ions are formed that they are injected into the vacuum chamber for detection and analysis. The geometry of prior art devices has been such that only a tiny percentage (sometimes as little as 0.01 percent) of the available sample ions reach the vacuum chamber. The remaining sample ions are wasted, reducing the sensitivity of the apparatus.

A further difficulty with many prior art devices is that the regions through which the sample flows, and in which ion-molecule reactions may occur, are in contact with duct and chamber walls through the mechanism of species diffusion. Ions and molecules therefore adsorb and desorb from these walls, leading to spurious signal drift and memory effects in the apparatus, unless temperature stabilized and (usually) heated inlet systems are used.

The present invention in one of its applications provides apparatus which increases sensitivity by increasing the number of desired ions transmitted into the vacuum chamber. In a preferred embodiment of the invention this is achieved by providing crossed fluid flow and electric fields which are arranged to concentrate the flow of desired ions from a relatively large region into a path of travel which carries them directly through the orifice or orifices into the vacuum chamber. At the same time, the crossed fields can in some circumstances be operated so as to cause other ions to follow different paths which do not carry them through the orifice, so that a partial separation is achieved. The combined concentration and separation steps result in an increase in sensitivity. In addition, the geometry of the preferred embodiment is such that the portion of the sample gas from which ions are formed may be kept largely away from contact with duct or chamber walls, thus reducing memory effects.

In a preferred embodiment of the invention a gas curtain is provided between the reaction chamber and the vacuum chamber. The gas curtain blocks transmission of the carrier gas into the vacuum chamber while permitting passage of ions from the trace gas. The gas used in the gas curtain is preferably cryogenically pumpable by conveniently obtainable temperatures, thus permitting the use of cryogenic pumping in the vacuum chamber. This allows an extremely high pumping rate and therefore allows use of a relatively large orifice for passage of the ions from the trace gas. This further increases the sensitivity of the apparatus, while at the same time considerably reducing its size and complexity. This improves the portability of the apparatus and permits versatility of operation, as will be explained.

The gas curtain of the invention, using cryogenically pumpable gas, together with cryogenic pumping in a connected vacuum chamber, may also be used for transferring other species, or solid materials, between a first gaseous medium and a second lower pressure gaseous medium, without significant transfer of one medium into the other, as will be explained further in the following description. This aspect of the invention may be used, for example for transferring into a vacuum a wire or tape on which trace gases or liquids have been absorbed, or it may be used (as will be explained) for transferring objects such as razor blades, or other articles arranged in a continuous strip, into or out of a vacuum for further processing. It may be used, for example, to transfer electrons from a vacuum into air, e.g. for electron beam welding, at atmospheric pressure, or it may be used as a windowless aperture for photons.

Further objects and advantages of the invention will appear from the following description, taken together with the accompanying drawings, in which.

Figure 1:
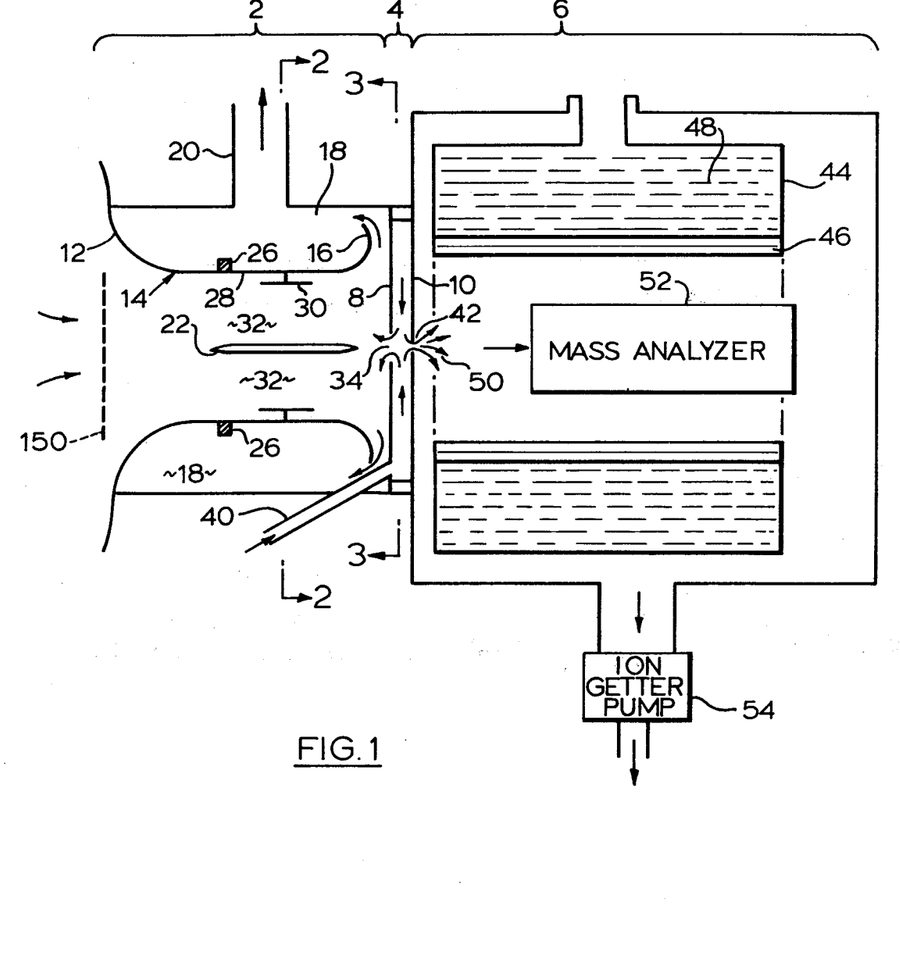
FIG. 1 is a diagrammatic view showing a preferred embodiment of the invention.
Figure 2:
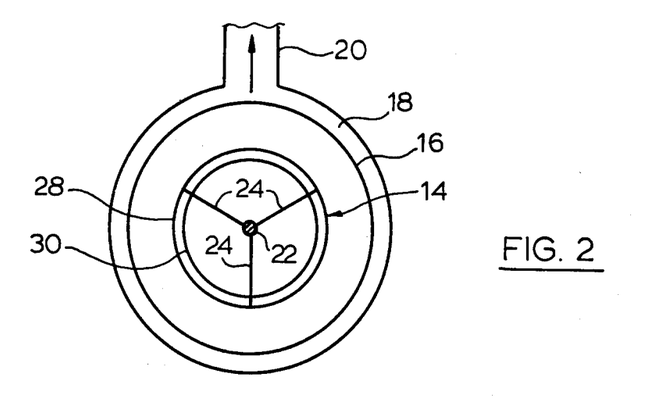
FIG. 2 is a sectional view along lines 2—2 of FIG. 1.

Reference is first made to FIGS. 1 and 2, which show typical apparatus according to the invention. Such apparatus includes an ion reaction section generally indicated at 2, a gas curtain section 4, and a vacuum chamber (and analyzing) section 6. The reaction section 2 and the gas curtain section 4 are connected by an interface plate 8, while the gas curtain section 4 and the vacuum section 6 are in turn connected by an orifice plate 10.

The reaction section 2 includes a bellmouth inlet 12 and a cylindrical duct 14 connected at 16 to a plenum 18. The plenum 18 is connected by duct 20 to a synchronous fan (not shown) which operates to draw the air or other gas to be analyzed through the bellmouth inlet 12 and into the duct 14. Settling screens (not shown) may be provided in advance of the inlet 12 to eliminate vortices and to help provide laminar flow.

Located in the duct 14 is a central axially elongated electrode 22. The electrode 22 is supported in a position aligned with the axis of duct 14 by a triangular spider of insulating material such as nylon thread 24, as shown in FIG. 2. A separate insulated wire, not shown, is used to apply a desired voltage to the electrode 22. The portion of the duct 14 which surrounds the electrode 22 is insulated from the bellmouth 12 by an insulating joint diagrammatically indicated at 26, so that the wall portion of the duct 14 downstream of the joint 26 forms a second or outer electrode 28. Located between the two electrodes 22, 28 is a ring-shaped ionizing device 30 such as a tritium foil.

Figure 1A:
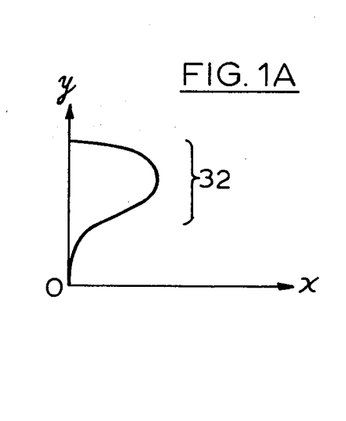
FIG. 1A is a graph of the ion creation region of the FIG. 1 apparatus.

In operation, air or other carrier gas containing the trace gas to be analyzed is drawn into the cylindrical duct 14 by the synchronous fan at a rate such as to provide a flow which is laminar but which is of sufficiently high velocity to minimize the effects of species diffusion. As the mixture passes the ionizing device foil 30, ion creation occurs in the region 32, forming a mixture of positive and negative ions in the gas. The ion creation region 32 is annular in form and its profile is shown in FIG. 1A, where distance from the foil is plotted along the Y axis (the foil being located at the origin) and the relative number of ions formed is plotted along the X axis.

During the ion creation, the beta rays from the tritium foil ionize components of the air or other carrier gas, resulting (after a series of reactions in the air or carrier gas) in the production of primary reactant ions. Some of the primary reactant ions then react with molecules of the trace gas to form product ions from the trace gas. This results in a mixture of product ions and reactant ions. From this mixture, the product ions are to be preferentially selected and analyzed.

An electric field, caused by appropriate potentials applied to the electrodes 22 and 28, the interface plate 8, and the orifice plate 10, is superimposed on the fluid flow. Ions are thus caused to drift with a local velocity $\vec{V_1} = \vec{V_f} + K\vec{E}$, where $\vec{V_f}$ is the local fluid velocity, $\vec{E}$ is the local electric field vector and $K$ is the mobility of the species in question. The potentials applied to the device, and the geometry of the device, are arranged (as will be explained in more detail presently) such that the desired ions of either sign and any mobility are caused to converge in an approximately conical fashion from the reaction region 32 to a central region downstream of the front of the central electrode 22 and generally aligned with the axis of the electrode 22. The desired ions are thence carried forward in a concentrated flux toward a central aperture 34 in the interface plate 8. A portion of the ions originating from the sample flowing through the reaction region 32 passes through the central aperture 34 in the interface plate; typically a flux concentration factor of between 60 and 100 may be achieved. Typical electric potentials, flow velocities and duct parameters that will achieve this flux concentration are described later in this description.

Figure 3:
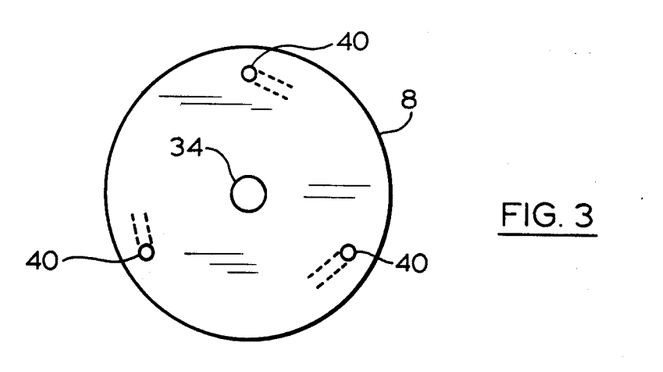
FIG. 3 is a sectional view along lines 3—3 of FIG. 1.

A second independent aspect of the invention will now be described, namely the transfer of the concentrated ions into the vacuum and analyzer section 6. This is accomplished by means of the gas curtain section 4 and by cryogenic pumping in the vacuum section 6. Specifically, the gas curtain section 4 is supplied with an appropriate gas (such as $CO_2$) which is selected to minimize reactions with the ions to be sampled and which can be conveniently cryopumped in the vacuum section 6. The curtain gas, which acts as a curtain or gas membrane between the reaction section 2 and the vacuum section 6, is directed into the gas curtain section 4 by inlet ducts 40 arranged to create a generally circular flow pattern having a circumferential component but directed generally radially inwardly in the gas curtain section 4 (FIG. 3). The curtain gas is supplied at sufficient flow to match the ingestion into the vacuum section 6 and to provide a small excess which effuses gently out through the central hole 34 in the interface plate 8, at sufficient flow to prevent passage of the carrier gas into the space between the interface plate 8 and the orifice plate 10. However, the concentrated ion flux is drawn forward, counter to this gentle outflow of curtain gas, by an appropriate attractive potential on the orifice plate 10, until these ions are caught up by the portion of the curtain gas flowing through the orifice 42 of the orifice plate and hence are carried into the vacuum section.

Figure 4:
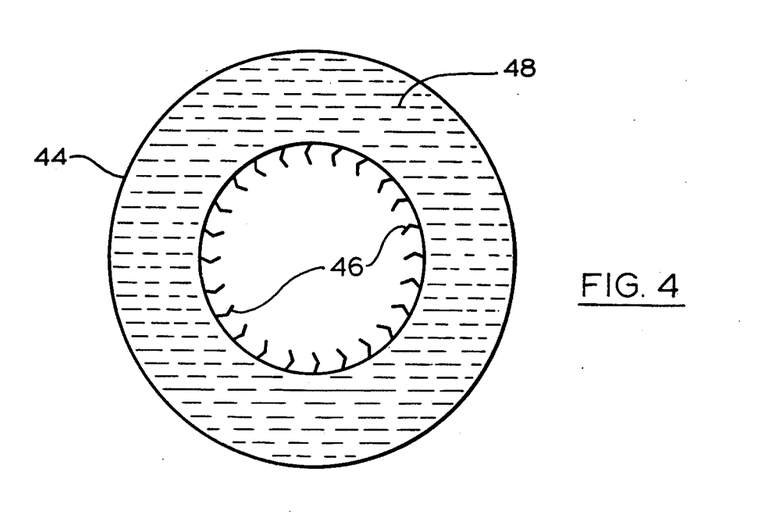
FIG. 4 is a sectional view of the cryogenic pump of FIG. 1.

The vacuum section 6 includes (see also FIG. 4) a cooling fluid reservoir 44 having fins 46. The reservoir 44 conveniently contains liquid nitrogen 48. As the curtain gas, containing the ions of interest, expands outwardly from the orifice 42, the molecules of $CO_2$ impinge on the fins 46 and deposit there, reducing the pressure in the vacuum chamber. The fins 46 are formed with appropriate trapping surface geometry, as is well known in the art of cryopumping, to maximize the trapping and depositing of the $CO_2$ molecules. By this means, an equivalent pumping speed of hundreds of thousands of liters/sec can be achieved, so that an operating vacuum in the $10^{-5}$ to $10^{-6}$ Torr range (suitable for mass spectrometry) can be obtained with an entry orifice 42 diameter of about 0.033 cm. This size is substantially larger than the 0.002 cm maximum or smaller size orifices conventionally used, so that the ion flux into the vacuum section can be increased by this invention at least by the ratio of hole areas, typically by several hundred or more.

Once a vacuum has been established (a mild vacuum may initially be created by convenient conventional means, e.g. a small mechanical roughing pump, and then increased by cryopumping), the ions of interest entering the vacuum section 6 expand in a free jet 50 and are focussed by appropriate electrostatic ion lens elements into a mass analyzer 52 such as a quadrupole mass spectrometer. The mass analyser 52 analyzes the ions according to their charge-to-mass ratio and allows quantitative determination by ion counting or other appropriate conventional techniques.

After the vacuum section has run for an appreciable period of time, $CO_2$ frost will build up on the fins 46 and defrosting will be required. Sufficient fin surface should therefore be provided to permit the vacuum section to operate for a sufficient interval before defrosting. In one prototype of the invention which has been operated successfully, operation was carried on for a full week before defrosting was required, but operation for a few hours will frequently be sufficient. In addition, a small additional vacuum pump 54 can be provided to remove non-condensable impurities (such as nitrogen) from the vacuum chamber. The pump 54 conveniently may be a getter ion pump.

Figure 5:
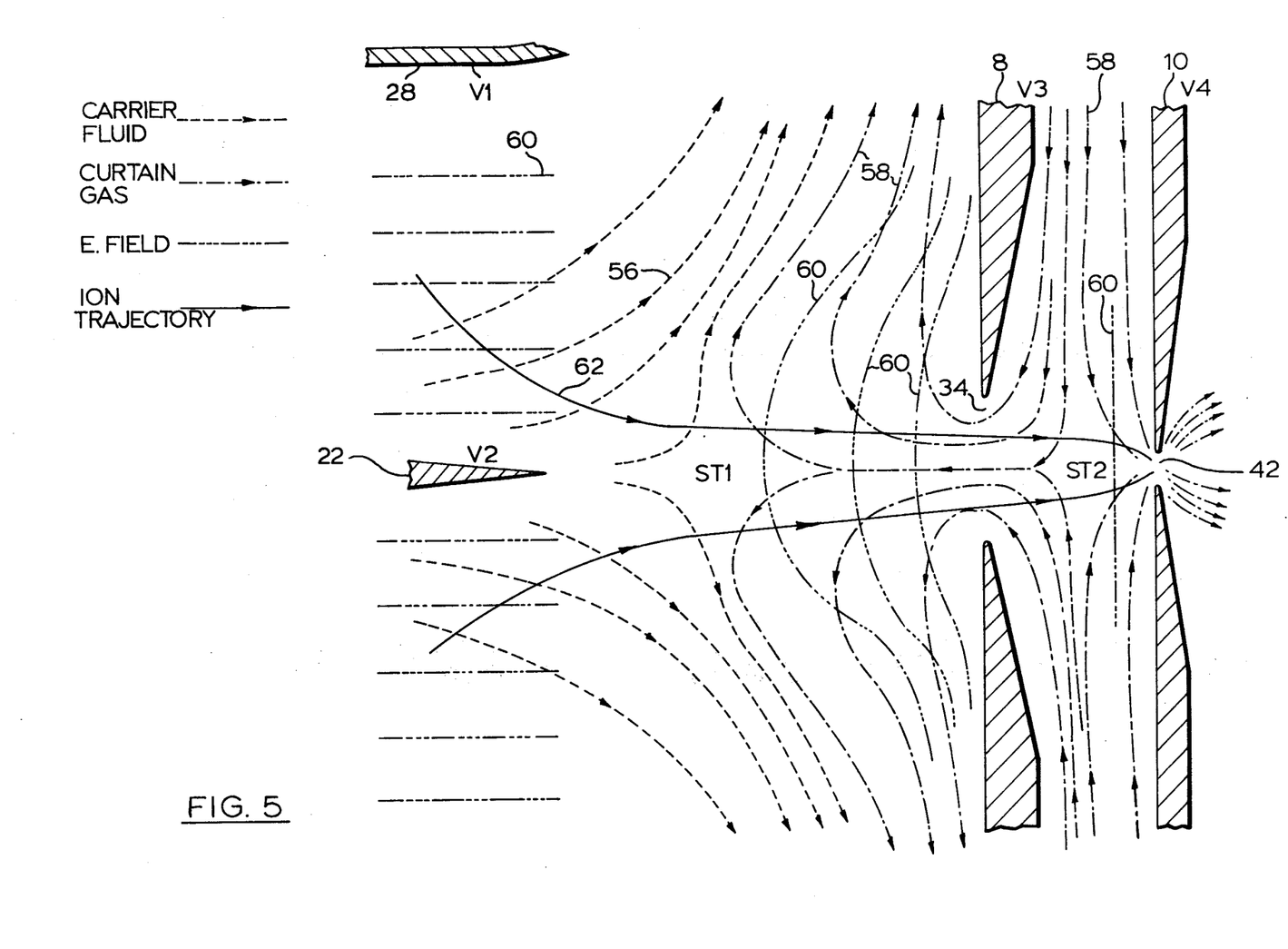
FIG. 5 is a graph showing fluid flow, electric field and ion paths.

The interaction of the crossed electric and fluid fields will now be described in more detail, with reference to FIG. 5. In FIG. 5, lines 56 represent the flow of the carrier fluid (usually air), lines 58 represent the flow of the cryogenic pumping fluid (e.g. $CO_2$), lines 60 are equipotential lines representing the electric field, and lines 62 represent the paths of the ions. Voltages $V1$, $V2$, $V3$ and $V4$ are applied to the electrodes 22, 28 and plates 8, 10 respectively. For analysis of positive ions, the voltages shown may all be positive, with $V1>V2>V3>V4$, as indicated in Table I at the end of this description.

It will be seen from FIG. 5 that in the region between the needle 22 and the encircling electrode 28, the electric field is essentially radial and the fluid flow lines are essentially axial. Thus, assuming use of the voltages shown in Table I, as sample ions are created, the positive ions move at an angle inwardly towards the needle 22 and axially towards the interface plate 8. The negative ions are immediately separated and are drawn towards the duct wall, reducing the amount of recombination. Ideally the positive ions just miss the tip of the needle 22 and are then drawn towards the aperture 34. Preferably the trajectories of the ions in the region between the needle and the duct wall converge conically towards a point just beyond the tip of the needle at an angle in the range between 30 and 60 degrees, preferably about 45 degrees. In the region downstream of the tip of the needle 22, the radial component of the electric field is small, so that radially inward movement of the ions is slight once they move downstream of the needle tip. However, the axial electric field between the needle tip and the plate 8 is quite substantial, so that the ions are drawn at high speed relative to the local fluid velocities, towards the aperture 34.

As the carrier fluid (e.g. air) approaches the interface plate 8, it is diverted radially outwardly, as indicated by the flow lines 56. In addition the cryogenic pumping fluid (e.g. $CO_2$) flowing from the aperture 34 in the interface plate meets the carrier fluid, creating a stagnation point ST1. At the stagnation point ST1 (which is on the central stagnation streamline) there is no movement of fluid. However, in the region of the stagnation point ST1, the axial electric field is sufficiently high to cause the ions to move forward through the stagnation point ST1, through the counterflowing cryogenic pumping fluid, and through the aperture 34.

When the ions enter the space between the interface plate 8 and the orifice plate 10, they encounter a second stagnation point ST2, created by the division of the cryogenic pumping fluid as it divides to pass through aperture 34 and orifice 42. The axial electric field carries the ions through stagnation point ST2 and they then pass through the orifice 42. It will be noted that because the carrier fluid does not pass through either aperture 34 or orifice 42, any materials in the carrier fluid that might normally tend to clog an orifice will not have that result in the embodiment here described.

It will be appreciated from the above discussion that the downstream tip of the needle 22 should be located upstream of the stagnation point ST1. If the tip of the needle 22 were located at or beyond the stagnation point ST1, then the fluid velocity at the tip of the needle would have no axial component or would be reversed, and the desired sample ions would all be drawn onto the needle 22 (rather than just missing the tip of the needle) and would be lost. Locating the downstream tip of the needle 22 upstream of stagnation point ST1 ensures that a number of ions will be carried forward through the stagnation point. Typically the spacing between the needle tip and the interface plate 8 is between about 3 and 8 cm, while the spacing between point ST1 and the interface plate 8 is about 1 or 2 cm.

In addition, it will be seen that when the ions enter the space between plates 8, 10, they then curve towards the orifice 42. The curved ion paths are caused by the flow of cryogenic pumping fluid into the orifice 42 and the superimposed electric field. To achieve this curved path effect, the voltages should be adjusted so that the speed of the ions due to the electric field as they pass through the space between the plates 8, 10 is not too high; otherwise the radius of the stream tube of ions drawn through the orifice 42 is unnecessarily reduced.

The embodiment described is capable of producing ion separation as well as ion concentration. In other words, if the ion creation process creates ions A and B, ions B being unwanted, it is possible to select fluid flow and electric field parameters that A/B in the stream entering aperture 34 is greater than A/B in the ion creation region. In one test made with apparatus of the invention, with ions A and B having masses of 18 and 182 a.m.u. (atomic mass units) respectively, a separation of 5.3 was obtained (i.e. A/B at aperture 34 was 5.3 times A/B in the ion creation region). The separation occurs since ions of different masses follow different trajectories, so that ions to be removed can in substantial numbers be directed onto the needle 22 or made to miss the aperture 34.

Figure 6:
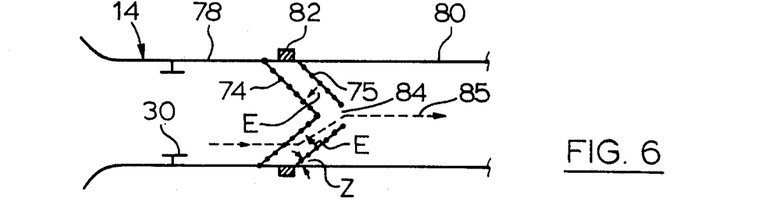
FIG. 6 is a sectional view of a modification of a portion of the FIG. 1 reaction section.

Although a preferred embodiment and application of the invention have been described, various modifications may be made. With reference to the reaction section 2, although the geometry shown in FIG. 1 is preferred, in which a central axial electrode is provided surrounded by an annular electrified duct wall, other geometries may be used if desired to provide an electric field having a component oriented transversely to the direction of fluid flow, to concentrate the desired ions away from the duct walls and in a region in which they will be carried forward by the fluid flow. For example, and as shown in FIG. 6, electrified screens or grids 74, 75 may be employed to create the necessary transverse electric field. The direction of the field produced by such screens is indicated by arrows E. The field is generally conical to produce convergence of the desired species. When the screens are used, each screen 74, 75 is preferably cone shaped, with screen 74 being electrically connected to duct portion 78 and screen 75 being electrically connected to duct portion 80. The duct portions 78, 80 are electrically insulated from each other by a short insulating portion 82, and the duct portion 80 is electrically separate from the interface plate 8 (not shown in FIG. 5). Thus, duct portion 78 and screen 74 may be held at one potential, duct portion 80 and screen 75 at another potential, and interface plate 8 may be held at a third potential.

Each screen 74, 75 is of very fine wire, and the downstream screen 75 typically has a hole 84 at its apex to facilitate passage of ions therethrough. The spacing between the screens, and the angles formed by the cones of the screens, may be adjusted to provide the desired ion trajectories. The wire used for the screens should be as fine as possible to minimize interference with the flow of the carrier fluid.

Figure 6A:
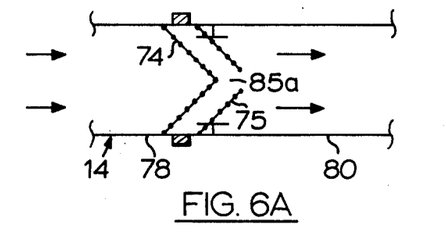
FIG. 6A is a sectional view showing a modification of the FIG. 6 apparatus.

For the FIG. 6 embodiment of the invention, a typical apparatus made according to the invention used 45 degree cones for the screens 74, 75 (i.e. the angle Z between each cone and the duct was 45°). The wire used for the screens was 0.1 mm in diameter, with mesh openings each being approximately 4 mm square, clear space. The screens were located 1 cm apart, measured normal to the surface of the cones. The above dimensions are illustrative only, but it will be appreciated that for good pre-separation to occur in the FIG. 6 embodiment, the screens 74, 75 should be fairly close together. The reason for this may be seen by observing the path 85 of a typical desired ion in the FIG. 6 apparatus. The path 85 has a portion located between the two cones. Different ions will have different paths between the cones, and if it is desired to select ions which travel parallel to the cones while they are between the cones, and to eliminate ions which have a more slanting path between the cones (in order to achieve a pre-separation), then the cones should be relatively closely spaced. As shown in FIG. 6A, the ring 30 may be placed to provide an ion creation region 85A between the screens 74, 75. This reduces the loss of ions due to screen 74. Other means (for example a single screen and appropriate potentials on the duct portions) may alternatively be used to create a generally conical E field.

The foregoing description has dealt with an embodiment of the invention which is suited for analyzing samples which are available in large quantities but in which the trace gases to be analyzed are present in very minute proportions. In some cases, the trace gas to be analyzed will be limited in quantity and may appear as a discrete region of higher concentration in a carrier gas. The trace gas and its carrier gas may emerge (see FIG. 7) for example from the tip of the outlet tube 86 connected to a gas chromatograph (not shown). A reagent gas, for example air, nitrogen, air with butane or methylamine or ozone, is introduced via inlet 12 into duct 14 at a flow which is approximately equal to the flow from tube 86. The flow velocities are adjusted to obtain the desired trajectories as before. Ionization is achieved as before by a tritium foil 88 located in the duct 14 surrounding the tube 86. The tritium foil creates reactant ions in the reagent gas. The reactant ions are focussed onto the central region and react with the trace gas to form product ions in the central region. A transverse electric field may be achieved as before by electrifying both the central tube 86 (which thus serves as the central electrode) and the surrounding duct 14, in order to concentrate the flux of the reactant ions onto the central region ions so that they may react with the trace gas. The ion flow in the central region will then pass through the aperture 34 in the interface plate 8.

Figure 7:
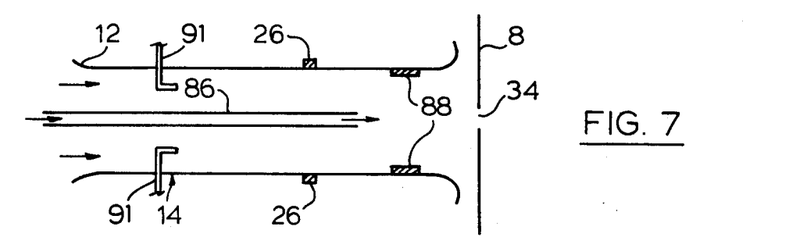
FIG. 7 is a sectional view showing a modification modification of the FIG. 1 reaction section.
Figure 7A:
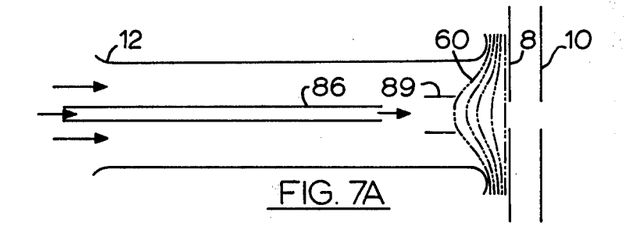
FIG. 7A and 7B are sectional views showing further modifications of the FIG. 1 reaction section.

A modification of the FIG. 7 apparatus is shown in FIG. 7A, where corresponding reference numerals indicate corresponding parts. In FIG. 7A the tritium foil 88 has been replaced by a tritium foil 89 of relatively small diameter encircling the stream of gas emerging from tube 86. Foil 89 is suspended by means not shown and is connected to a source of potential, as are interface plate 8 and orifice plate 10, to create electric field lines as shown at 60 in FIG. 7A. Typical potentials for negative ion operation are: foil 89, −2000 volts; plate 8, −200 volts; and plate 10, −130 volts. The small ring 89 provides efficient use of the beta rays for creating ions, and the field 60 directs the ions through the aperture 34. Tests have shown the FIG. 7A arrangement of ring and field to be quite effective in producing ions and in directing them through aperture 34.

Figure 7B:
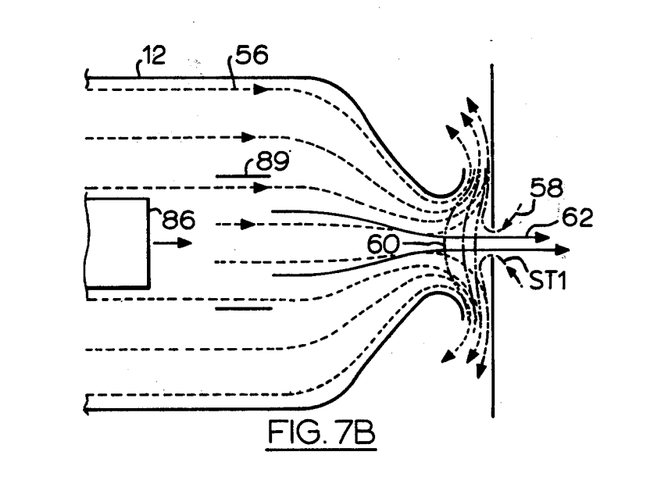

Reference is next made to FIG. 7B, which shows a modification of the FIG. 7A apparatus. In FIG. 7B, the duct 12 narrows smoothly in diameter adjacent the interface plate 8, as indicated at 91 in FIG. 7B. The carrier fluid (e.g. air) in the duct 12 follows a path as indicated by streamlines 56. It will be seen that the streamlines 56 have all contracted, giving a form of concentration. When the carrier fluid approaches the interface plate 8, the streamlines 56 spread out again. However, the electric field at the aperture 34 (indicated by lines 60) is made strong enough to prevent the reduced diameter stream tube of ions (whose path is indicated by lines 62) from spreading out appreciably. For this purpose the field strength is adjusted so that the ion drift velocity is typically at least 3 to 5 times the local fluid velocity, although these values may vary depending on the parameters of the system. The result is that the narrow stream tube of ions is funnelled through the aperture 34.

The stagnation point ST1 upstream of the aperture plate 8 in the FIG. 7B embodiment is very close to the aperture plate 8. It will be seen from FIG. 7B that the electric field (produced by potentials on plate 8 and in the walls of duct 12) is such that there is a component of the field transverse to the direction of gas flow, at a location upstream from stagnation point ST1.

The above described contraction of the stream tube containing the ions can substantially increase the ion signal transmitted into the vacuum chamber. For example, a 10 to 1 reduction in the diameter of the ion stream tube will result in a 100 times increase in the number of ions per unit area. It will be understood that the contours of the reduced diameter portion 91 of duct 12 should be designed so that laminar flow is preserved; this form of design is well known to those skilled in the art. Allowance will also be made for the effusion of curtain gas 58 from the aperture 34, in the design of the narrowed portion 91.

The concentration method shown in FIG. 7B may be used not only with the FIG. 7 or 7A apparatus, but also with the FIG. 1 apparatus, since the stream tube of ions leaving the needle 22 can still benefit from a reduction in diameter. It may also be used with the FIG. 1 apparatus with the needle 22 completely removed and with the ring 30 reduced in diameter and made like the ring 89 of FIG. 7A, or it may be used in the FIG. 6 apparatus, with the conical screens 74, 75 or with these screens replaced by a ring such as ring 88 of FIG. 7.

If desired, other reactive media such as butane gas, nitric oxide, methylamine, ozone, etc. may also be introduced into the carrier gas of the FIG. 1 apparatus or in the other apparatus described, to modify the ion molecule reactions to increase the sensitivity of the apparatus for desired species. Such reactive media may be added for example via inlet ducts 90 shown in FIG. 1 or inlet ducts 91 shown in FIG. 7.

Figure 8:
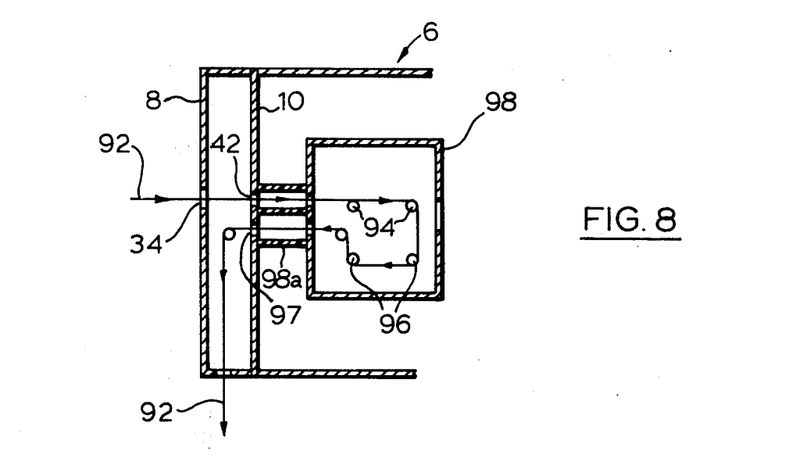
FIG. 8 is a diagrammatic view showing the use of the invention with a tape or wire material carrying medium.

Instead of providing a gaseous ion input to the gas curtain section 4 and vacuum section 6, the input may be in the form of a tape or wire 92, as shown in FIG. 8. Ions of the desired sign may be focussed onto the tape or wire 92, where they are neutralized. Provided that the wire or tape 92 is surfaced with an appropriate material, such as graphite for organic ions, or with appropriate metals, zeolites, metal oxides, the former ions will be adsorbed on the surface of the tape or wire and will remain there until the tape or wire is heated. With appropriate selection of materials, simple adsorption of the trace molecules without prior ionization is a selective process and may also be employed. If desired, components of liquids, e.g. from a liquid chromatograph, may be adsorbed onto the tape or wire by conventional techniques, for analysis in the vacuum chamber. The tape or wire 92 is then fed through the aperture 34 in the interface plate 8 and through the orifice 42 in the orifice plate 8, into the vacuum chamber 6. In the vacuum chamber the tape or wire 92 passes around capstans 94 which are electrified to pass current through the section of tape or wire between them, heating the tape or wire to drive off the adsorbed species bound thereto. The tape or wire 92 may then be returned via rollers 96 through an orifice 97 into the gas curtain and may be wound on a storage reel (not shown). Alternatively the tape or wire 92 may form an endless loop. A small hood 98 may be placed around the orifice 42 to generate some pressure within the hood, typically 0.2 to 5 torr, which is approximately the pressure required for chemical ionization reactions. Chemical ionization reactions may then be employed within the hood 98 to reconvert the desorbed molecules into ions. The hood 98 is typically insulated from the plate 10 by an insulating support section 98a.

It will be seen that by using the tape or wire 92, traces of gases in air or other gases, or liquids may in effect be tape recorded, stored, and then played back by placing them in the apparatus of the invention which then serves as a readout station. The reaction section 2 of FIG. 1 may if desired be used to create and concentrate ions from a trace gas into a central region where they may be captured by a tape or wire.

Although the use of $CO_2$ as a curtain gas has been described, other gases may also be used, provided that they have a low reactivity for use in positive or negative ion studies and provided that they can be cryo pumped at a conveniently obtainable temperature. In some cases, gases of high reactivity may be acceptable, for example ordinary $H_2O$ (steam). Alternatively, various freon gases which are low reactivity may be used. However, since a small amount of curtain gas diffuses out the aperture 34 in the interface plate 8, the gas used should normally be acceptable in a room or means provided to remove it. The flow of the curtain gas need not contain a circumferential component but may be purely radial. Preferably the curtain gas used should be a gas which, when deposited in solid phase, has a vapour pressure of less than $10^{-4}$ Torr at a temperature attainable by the cryo pumping surfaces.

Figure 8A:
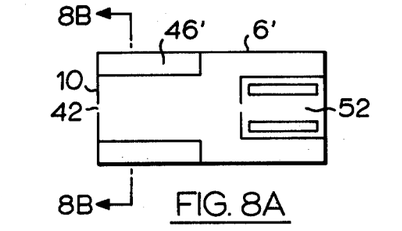
FIG. 8A is a sectional view showing a modified vacuum chamber arrangement.
Figure 8B:
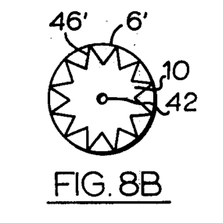
FIG. 8B is a sectional view along lines of FIG. 8A.

If desired, mechanical refrigeration may be used instead of using liquid nitrogen. In this event, a wider range of curtain gases may be used. By way of example, very low temperature refrigeration units are currently produced by Cryogenics Technology Inc. (CTI), of Waltham, Mass., U.S.A. Some of these coolers can remove several watts of heat at temperatures as low as 20° K. This makes it possible to use gases such as argon, krypton (if available), or nitrogen as the curtain gases. FIGS. 8A and 8B show a typical vacuum chamber 6' having corrugated fins 46' extending around its periphery and suitable for use with mechanical refrigeration. The fins are of highly conductive metal, e.g. nickel plated copper, and are connected directly to the cold bar (not shown) of a suitable heat pump such as one made by CTI, above. A second cooling surface (not shown) may be provided encircling chamber 6' and may be connected to a second cooling point on the pump. The mass analyzer 52 may be located in a portion of the chamber 6' behind the fins 46'. Not shown is the insulation in which the vacuum chamber is packed.

When very low temperature mechanical cooling is used, the gas curtain could in some cases be eliminated and instead the air itself could be pumped. However, the use of a gas curtain is much preferred since (1) if the air were pumped, an auxiliary pumping mechanism would be needed to remove helium and hydrogen; (2) the gas curtain permits substitution, in place of air, of a purified gas (e.g. argon) of low reactivity which reduces the complexity of the possible reactions (such as switching and clustering reactions) when ions are being transferred through the curtain gas; (3) clustering reactions, which are particularly promoted by rapid expansion in a free jet, are reduced by the use of a low reactivity curtain gas; (4) an optimum gas can be selected for the gas curtain depending on whether positive or negative ions are being detected (argon for example is an excellent choice for both); (5) particulates in the air, which tend to clog the very small orifices used, are not permitted to pass through the orifices.

It will be appreciated that instead of cryo pumping the curtain gas, other means for evacuating the chamber may be used (e.g. large mechanical pumps). The advantages listed above for using curtain gas still apply. Other relatively low reactivity curtain gases may then be used, such as neon.

Figure 9:
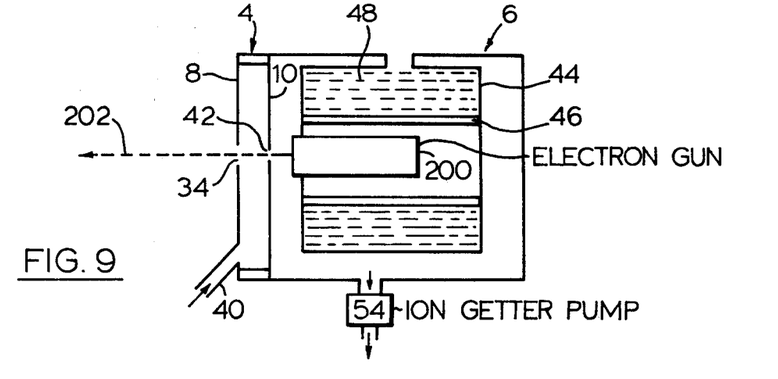
FIG. 9 is a sectional view showing an application of the FIG. 1 gas curtain and vacuum chamber portions.

Although the invention has been described for use in connection with trace gas analysis, the technique of the invention, by which species or materials may be transferred into a vacuum using a curtain gas and cyrogenic pumping, may be used in other applications. For example, razor blades during their manufacture may need to be transferred to a vacuum to be metal coated. In accordance with the invention, uncut razor blades in the form of a continuous strip may be transferred through the aperture 34 in the interface plate 8 and through the orifice 42 in the orifice plate 10 into the vacuum chamber. In such event the aperture 34 and the orifice 42 will take the form of narrow slits. The same procedure may be used for transferring the strip material from the vacuum chamber, using another aperture in the gas curtain or by using another gas curtain. Any strip material may be so transferred, for example strip material requiring vacuum deposition. Other bulkier items may also be fed through the aperture 34 and orifice 42 into the vacuum to be treated, so long as they are fed in the form of a continuous strip (if necessary with spacers between them), and so long as the gap between the edges of such strip and the border of the orifice 42 is kept to a minimum. The gas curtain and cryogenic pumping technique may also be used to provide a windowless aperture for electrons, photons, or any other species directed towards the aperture from either direction. An example of such application is illustrated in FIG. 9, which shows the gas curtain section 4 and the vacuum chamber 6. In the vacuum chamber 6, the mass analyzer 52 and associated lenses have been replaced by an electron gun 200 which directs a beam of electrons (indicated by line 202) through orifice 42 and aperture 34 into the atmosphere. The electron beam 202 may be used for example for electron beam welding. The orifice plate 10 may be connected to an appropriate potential to attract the electrons through the orifice 42, while the gas curtain section 4 may use the same cryo pumpable gas (e.g. $CO_2$) as described in connection with the mass analyzer application of the invention.

The technique of the invention may also be used to transfer species or materials between two gaseous media, one at lower pressure than the other, without significant transfer of one medium into the other. For example, it may be used to transfer a strip of material from air into low pressure pure nitrogen or into a low pressure inert gas, using water vapour or an appropriate freon gas as the curtain gas, and using dry ice or other appropriate material (or even ordinary refrigeration coils) as the cooling means for cryo pumping the curtain gas.

Reference is next made again to the FIG. 1 (or FIGS. 6, 7A, 7B) embodiment of the invention. In the reaction region of this embodiment, certain numerical values are desirably observed in order to maximize the performance of the equipment. For example, when a tritium foil is used as the ionizing source, the diameter of the inlet duct 14 will normally be sufficiently great to allow the tritium foil 30 to establish an ionization region inside the diffusion boundary layer on the duct wall. The duct 14 is preferably therefore at least 10 cm. in diameter, for optimum efficiency, when a tritium foil is used as the ionizing medium. Other ionizing devices may of course be used if desired.

In addition, the rate of sample gas flow through the tube should not normally exceed an upper limit set by the critical Reynolds number since turbulent flow may then result, leading to instabilities in the spectra of ±10 percent or more. The sample gas flow will therefore usually be limited to values that will produce laminar flow (i.e. usually a Reynolds number of 2000 or less, although with appropriate duct configurations laminar flow can sometimes be obtained at a higher Reynolds number).

It is also desirable that the fluid velocity not be too low. If the fluid velocity is too small, the diffusion boundary layer at the edges of the duct 14 becomes large and fills the duct, and fully developed pipe flow occurs. Molecules and ions can then diffuse onto the walls of the duct 14 and off again, resulting in the memory effects which the invention attempts to avoid. In addition, since at low fluid velocity the ions remain in the fluid field longer and diffuse to a greater extent, resolution is lost in the separation effect. It should also be noted that when the gas velocity is reduced, then the electric field must also be reduced in order to achieve the desired concentration effect, but since diffusion remains constant despite the reduced flow and electric field, this tends to cancel the concentrating effect. Therefore, the fluid velocity and electric fields should be maintained as large as possible consistent with laminar flow. Preferably the fluid velocity will not be less than 300 cm. per minute in any of the devices described, in regions in which ions are being handled, and it will normally be considerably higher than this, typically about 600 cm per minute or more (the upper limit being that of turbulent flow, as discussed).

For the curtain gas section, sufficient flow should be provided to equal the amount ingested into the vacuum section and to provide an excess flow which will typically be 1 to 5 cubic centimeters per second. The following are typical flows which may be used.

TABLE I

| Orifice 42 Diameter | Curtain Gas Flow Into Vacuum | Excess Flow |
|---|---|---|
| .006 centimeters | .46 cc. per second | 1 to 5 cc. per second |
| .012 centimeters | 1.9 cc. per second | 1 to 5 cc. per second |
| .025 centimeters | 7.6 cc. per second | 1 to 5 cc. per second |

A typical aperture 34 for the interface plate 8 is 0.32 centimeters, for a prototype instrument made in accordance with the invention.

Typical spacing between the interface plate 8 and the aperture plate 10 may be 3 to 4 mm, but larger or smaller spacing may also be used.

In a typical device made in accordance with the invention, and using a quadrupole mass spectrometer 99, (FIG. 10), curved focussing screens 100 may be used, together with electrostatic lens elements 102, to focus the ions through the inlet aperture 104 in the casing of the spectrometer 99. Typical potentials used in equipment made according to the invention are shown in Table II below. All potentials shown are referenced to ground and were used for collection of positive ions.

TABLE II

| | | |
|---|---|---|
| V1 : + 2800 | to + 3600 | V6 : − 90 |
| V2 : + 1400 | to + 2000 | V7 : − 90 |
| V3 : + 50 | to + 1500 | V8 : − 90 |
| V4 : 0 | to + 120 | V9 : − 120 |
| V5 : 0 | | |

Figure 10:
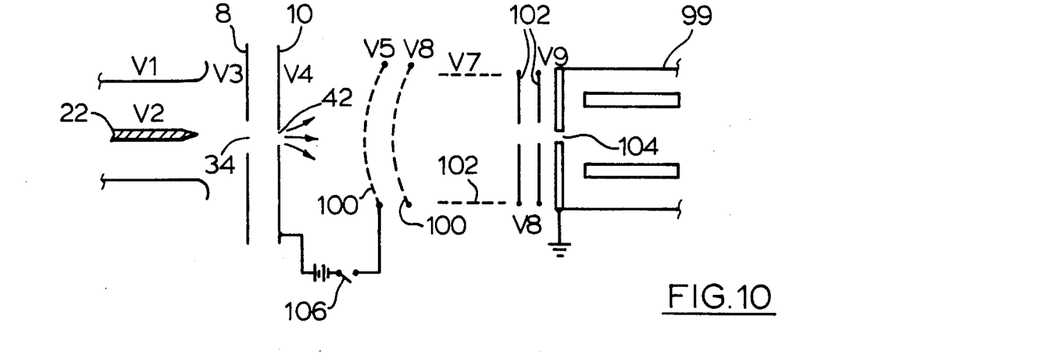
FIG. 10 is a diagrammatic view showing electrostatic focussing elements which may be used when the invention is used with a quadrupole mass spectrometer.

It will be noted that with the apparatus of the invention, the ions to be analyzed are formed gently, for example by simple transference of charge to them, rather than being impacted with electrons. Therefore, the number of fragments to be analyzed is much reduced as compared with typical conventional mass spectrometers. However, if desired, a field can be applied to the ions within the vacuum chamber in order to accelerate them in regions in which the cryogas density is sufficiently high to permit energetic ion molecule collisions which will fragment the ions. For example, a 100 volt potential difference may be applied between the orifice plate 10 and the first screen 100 to accelerate and fragment ions. A simple switch 106 may be employed to switch the accelerating voltage on or off, so that either the intact ions, or their fragments, may be analyzed in the mass spectrometer 99. This flexibility may be combined with the added capability of positive and negative mode analysis, by providing another switch (not shown) to apply voltages appropriate for analysis of negative ions. Thus the operating mode of the apparatus may readily be switched.

Although the aperture 34 and orifice 42 have been shown as aligned with the common axes of the needle 22 and duct 14, the axial alignment shown may be altered in some applications of the invention (e.g. transfer of a tape or wire into the vacuum chamber); in that case the aperture 34 and orifice 42 may if desired be substantially misaligned.

It will be further appreciated that the crossed fluid and electric field technique described may be achieved with other configurations of both fluid and electric fields, e.g. by use of Einzel lenses. Further, the crossed fluid and electric field arrangement may be used for focussing ions into conventional vacuum chambers, or for focussing the ions onto any other desired target (such as a detector electrode), without the cryo pumpable gas curtain, but of course use of the cryo pumpable gas curtain is much preferred.

It will be appreciated that naturally occurring ions in air are not normally observed with the apparatus of the invention, since they are unable to enter the flow duct due to the strong electric fields present. However, the apparatus can be operated in such a manner as to observe naturally occurring ions, by alternately removing and applying the previously described potentials. The ionizing source should not be in place in this application. The periodicity of the pulsing mode should be adjusted so that the field is turned off long enough in each cycle to allow the naturally occurring ions to fill the flow duct, so that they will be available for analysis when the field is turned on in each cycle.

Figure 11:
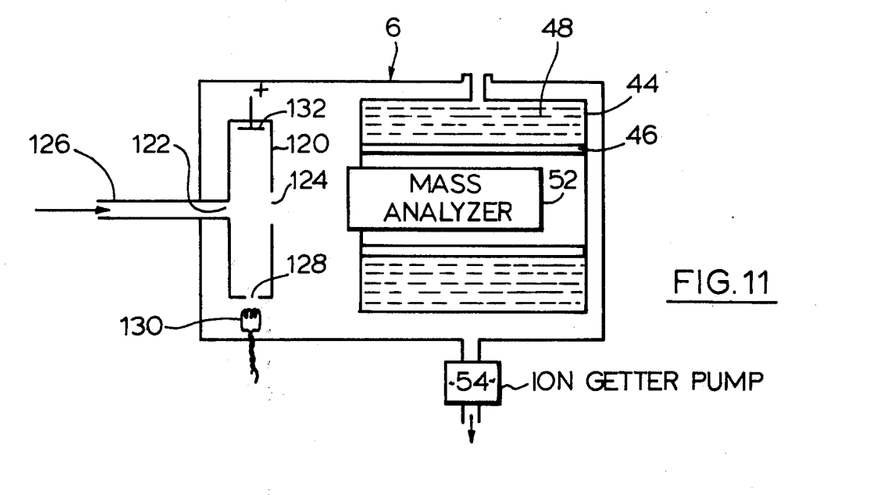
FIG. 11 is a diagrammatic view showing a further embodiment of the invention in which the carrier gas is a reagent gas and is cryo pumpable.

A further embodiment of the invention is described in FIG. 11. FIG. 11 shows the vacuum chamber 6 as containing a hood 120. Hood 120 has an inlet 122 and an outlet 124. Connected to the inlet 122 is an inlet conduit 126 through which is fed a cryo pumpable chemical reagent carrier gas containing the trace gas to be analyzed. The feed to conduit 126 may be for example the effluent of a gas chromatograph which uses isobutane as a carrier.

Hood 120 includes a small orifice 128 through which electrons are directed from a filament 130, the electrons being captured by plate 132. The hood 120 and associated parts form a standard chemical ionization source, except that the outlet orifice 124, and hence the ion flow, may be made several hundred times larger than has previously been possible, through cryo pumping the reagent carrier gas. The vacuum chamber 6 is typically the vacuum chamber 6 of FIG. 1, including the cooling reservoir 44. The lens elements of FIG. 9 may be used to focus the ions from the hood 120 onto the entrance aperture of the mass analyzer.

When the apparatus of FIG. 11 is operated in the chemical ionization (CI) mode, the pressure inside the hood 120 should be between 0.2 and 5 Torr. This pressure is achieved, even though the outlet orifice 124 is of substantial area, by ensuring that a sufficiently high flow of material is directed into duct 126. For operation of the FIG. 11 apparatus in the electron impact (EI) mode, in which ions are created primarily by electron impact, and which operates at pressures of $10^{-4}$ Torr or less, a lower quantity of material is fed into duct 126. The same device may then be used for operation in the CI or EI mode.

If desired, the present invention may be employed to observe gases adsorbed on the surface of particles. Adsorbed gases on particles are readily driven off by application of heat, and therefore a heater, indicated in dotted lines at 150 in FIG. 1, may be provided to heat the air entering the duct 14. A first measurement can then be taken with the heater 150 off, and a second measurement may be taken with the heater 150 on. The difference between the two measurements will represent gases adsorbed onto the surfaces of particles and driven off by the heat. Alternatively, a filter 151 (FIG. 1) may be placed in the duct to collect particulates over a period of time, and then heat applied via the flowing air stream or substituted purified carrier gas to desorb the gases adsorbed on the collected particulate matter.

In the application of the invention involving transfer of ions into a vacuum chamber through a gas curtain consisting of a cryogenically pumpable gas, loss of ion signal may occur for the following reason. When the gas of the gas curtain expands through orifice 42 in a free jet, it undergoes an enormous temperature drop due to its expansion. The temperature drop can result in consensation of curtain gas molecules about some of the desired ions in the region of the free jet. Such clustering is to be avoided because (1) it masks the true mass of the ion, i.e. it complicates interpretation of the spectra, and (2) it makes focussing and detection more difficult.

To deal with this problem when it occurs, this invention provides three approaches. One is the use of an appropriate curtain gas, e.g. ultra pure argon, which reduces clustering drastically as compared with air. The second approach is the use of an appropriate E/N (field strength to gas number density ratio), not enough to fragment the original ions but sufficient to maintain the ion molecule collision energies at values which inhibit clustering. This approach will be described in more detail shortly.

Figure 12:
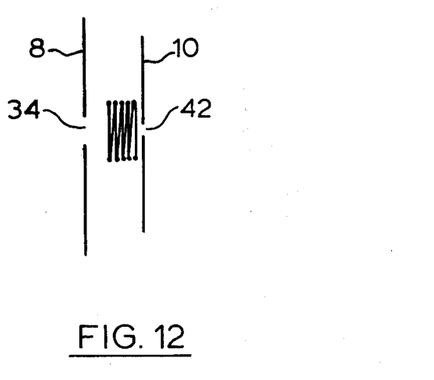
FIG. 12 is a side view showing a heater which may be used in the apparatus of FIG. 1.
Figure 13:
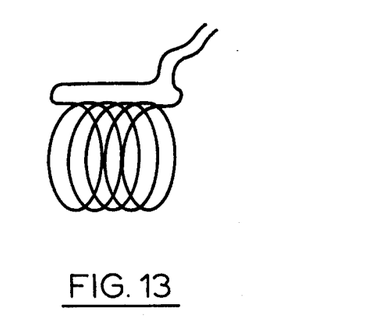
FIG. 13 is a perspective view of the heater of FIG. 12.

The third approach, which will now be described, is to heat the curtain gas prior to its expansion through the orifice 42. Typically the temperature of the curtain gas entering orifice 42 will be raised to approximately the range 90° C to 130° C (sufficient to inhibit clustering but low enough to avoid decomposing the ions). If desired, only that portion of the curtain gas which enters orifice 42 (a flow of 1 to 10 c.c. per second) may be heated. To this end, and as shown in FIGS. 12 and 13, a small heater winding 152 may be placed in the space between plates 8 and 10, around orifice 42. The heater winding 152, which is energized through leads 154, consists of fine heater wire which will not appreciably interfere with the flow of curtain gas through it. The sensible heat transferred into the curtain gas (less than a watt) imposes only a small fractional increase to the heat load on the cooled surfaces of the vacuum chamber. Alternatively, all of the curtain gas may be heated to inhibit clustering during transfer of the ions through the curtain gas.

Figure 14:
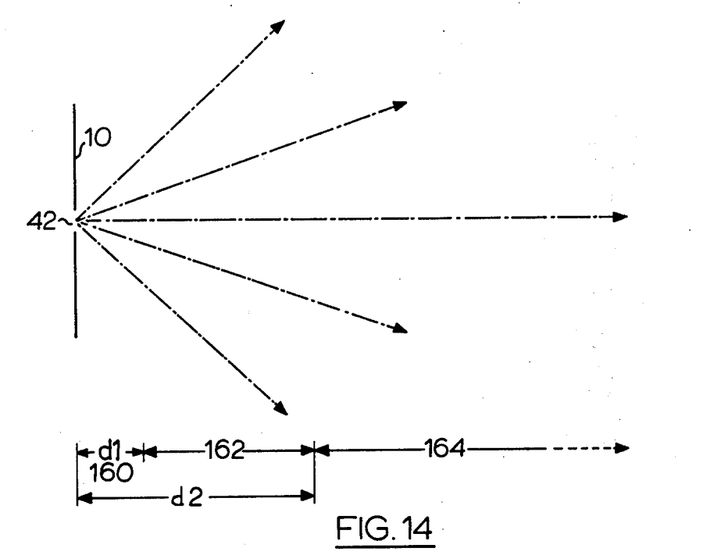
FIG. 14 is a sectional view showing certain regions in the vacuum chamber.
Figure 15:
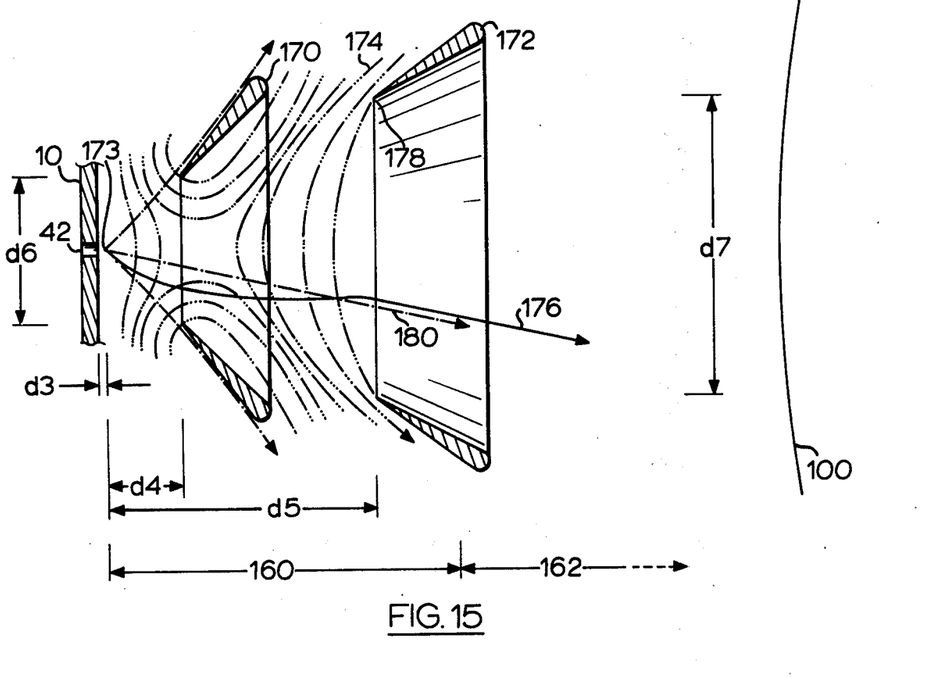
FIG. 15 is a sectional view showing an arrangement of focussing elements, in one of the regions of FIG. 14.

Reference is next made to FIGS. 14 and 15, which illustrate the second approach introduced previously. This feature deals with the problem of focussing the ions as the curtain gas in which they are contained expands in the vacuum chamber 6. It is desirable to focus the ions so that as many as possible reach the mass spectrometer, but it has been discovered that conventional focussing (by appropriate potentials) can impart so much kinetic energy between collisions to the ions that they tend to fragment upon collision, rendering analysis more difficult in some cases. Also, conventional focussing can impart an undesirable energy spread to the ions which affects resolution and detectability achievable in some mass analyzers such as the quadrupole mass spectrometer.

The expanding curtain gas jet, indicated at 158 in FIG. 14, may be characterized as having three regions, indicated at 160, 162, 164 in FIG. 14. In region 160 the gas jet, although rapidly expanding, is still relatively dense. In this region, electric fields can be applied to alter the trajectory of the ions. The electric field E in region 160 is selected to yield E/N values which meet the following criteria:

(1) large enough to affect the ion trajectories in the desired manner, (2) not so large as to fragment the original ions through the energy acquired by the ions through the electric field between collisions.

The resultant thermal energy imparted to the gas cloud in region 160 by application of the field is negligible. In general, region 160 may be defined as the region in which the ions cannot acquire an energy greater than about 0.5 ev (electron volts).

In region 162, the density of the gas jet is much reduced, and the ions are able to pick up substantial additional energy if an electric field is applied to yield appropriate E/N values. At the same time, there are enough gas molecules present so that some collisions can occur. In general, region 162 may be defined as a region in which the ions can acquire energy greater than 0.5 ev, and in which charge transfer, fragmentation or other collisional activation may occur.

The third region 164 may be referred to as the vacuum trajectory region. Here, the gas molecules are essentially gone; the likelihood of collisions between ions and gas molecules is therefore very low, and this is the region in which the focussing screens 100 and the electrostatic lens elements 102 (FIG. 10) are used. Region 164 is in other words a region of free molecular flow; the mean free path of ions in region 164 is of the order of a few centimeters or greater (typically 2 cm or more).

As shown in FIG. 15, advantage of the existence of the regions can be taken by providing appropriate focussing elements in region 160. In region 160, the curtain gas (and with it the ions) is expanding in a wide cone, most of the ions however being contained within a 90° whole angle cone because the flux of ions is distributed according to a cosine squared law. Accordingly, an electrostatic lens is provided, formed by two conical tapered rings 170, 172. The rings 170, 172 are supported by fine wires (not shown) and are aimed approximately at the orifice 42 to minimize interference with the expanding gas. Since the actual expansion of the curtain gas occurs in a cone whose vertex is displaced slightly outwardly from the orifice plate 10, the cones subtended by the rings 170, 172 may in fact have their vertices at an origin or point 133 spaced slightly outwardly of the orifice plate 10 (by less than 1 orifice diameter).

When appropriate potentials are applied to the rings 170, 172 relative to the orifice plate 10, a saddle shaped field can be created, indicated by field lines 174 (which of course show the field only in two dimensions). The trajectory of a typical ion is indicated at 176. Ions whose initial trajectories are outside the rings 170, 172 are lost, but these ions are very few in number. Ions whose initial trajectories are at less than 45° to the axis of the system are deflected inwardly until after they have passed the leading edge 178 of cone 172. At this point, the field of the rings ceases to affect the ions. The ions now enter region 162 and assume the direction of movement of the expanding gas jet 180. The result of this is that the ions initially in a 90° whole angle cone are concentrated into a much smaller whole angle cone, e.g. about 30° to 45°, so that more of the ions can be focussed in region 164 so as to travel into the mass spectrometer.

Figure 16:
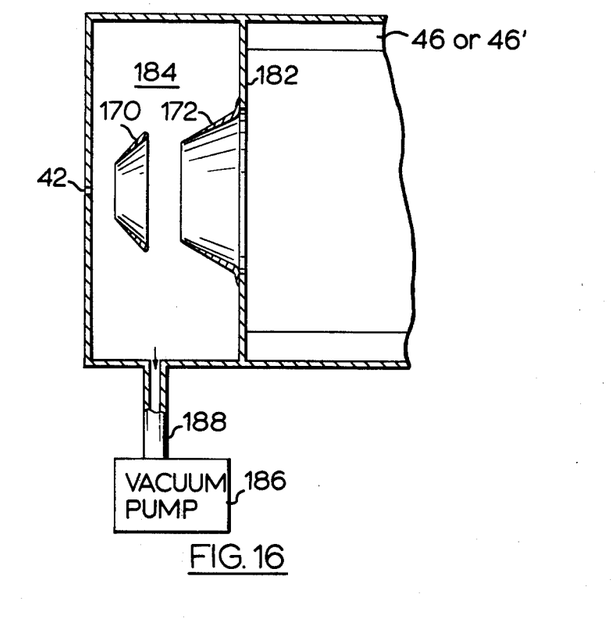
FIG. 16 is a sectional view showing a modification of the FIG. 15 structure.

An added advantage of the approached described above results from the fact that a substantial separation of the ions from the gas flow has been achieved at relatively high pressures. Therefore, pressure staging can be utilized to pump away the large fraction of the gas flow external to the cone into which the bulk of the ions have been focussed. An example of such pressure staging is shown in FIG. 16, where the second ring 172 is extended and mounted on a separator plate 182 to form a plenum 184 in region 160 and from which gas can be pumped at relatively high pressure with a small volumetric capacity pump 186 (typically of the order of 1 ton and a few liters per second). Gas is exhausted from the plenum 184 to the pump 186 via a duct 188. This reduces the load on the vacuum pump means (usually a cryopump) used for the remainder of the vacuum chamber. This permits a larger orifice for a given size of cryopump, or a smaller cryopump for a given orifice size. The plenum 184 is of course not cryo cooled; cryo-cooling is reserved for the region downstream of ring 172.

The dimensions of regions 160, 162 will vary depending on the size of orifice 142, and the strength of the electric fields applied in region 162 (at high fields, region 162 begins closer to orifice plate 10 since a higher field can impart 0.5 ev to an ion in a shorter distance than can a lower field). For an orifice diameter of 0.017 cm, Table II below gives typical approximate dimensions (it will be realized that these are not to be taken as limiting):

TABLE II

| | | |
|---|---|---|
| d1 | (axial distance from orifice plate 10 of boundary between regions 160, 162) | .5 to 1.5 cm |
| d2 | (axial distance from orifice plate of boundary between regions 162, 164) | 6 to 7 cm |
| d3 | (distance of origin from orifice plate 10) | zero to .014 cm (0 to .85 orifice diameter) |

TABLE II-continued

| | |
|---|---|
| d4 (distance between origin 173 and leading edge of ring 170) | .17 cm (10 orifice diameters) |
| d5 (distance between origin 173 and leading edge of ring 174) | .6 cm |
| d6 (diameter of leading edge of ring 170) | .3 cm |
| d7 (diameter of leading edge of ring 172) | .7 cm |
| Angle from axis of ring 170 | 45 degrees |
| Angle from axis of ring 172 | 30 degrees |

Screens such as screen 100 (shown in FIG. 15) to accelerate ions to produce interactions may be placed anywhere in region 162. Typical voltages used are as follows: if Va is the voltage on the orifice plate, Vb the voltage on ring 170, Vc the voltage on ring 172, and Vd the voltage on accelerating screen 100, then (for positive ions);

$Vb > Va \geq Vc \geq Vd$

Typical voltages may be (for positive ion operation):
Va: +105 volts
Vb: +110 volts
Vc: +70 volts
Vd: −150 volts The focussing means described with reference to FIG. 15 may be used in conventional instruments (in which there is no curtain gas and ordinary vacuum pumps are used), and it may be used with other kinds of equipment in which ions to be detected are carried into a vacuum chamber together with an expanding gas jet.

By judicious choice of voltages Va, Vb, Vc, Vd, clustering reactions can to some extent be controlled. In region 160, even though the ions cannot acquire more than 0.5 ev, they do acquire some energy. The energy can be controlled to reduce the likelihood of ions and molecules sticking together (clustering) when they collide, and to break apart some clusters that are bound loosely together by very low energy bonds (less than 0.5 ev). The geometry of region 160 (i.e. the spacing, dimensions and angles) of rings 170, 172 or of any other appropriate lens elements used, may also be varied depending on the application of the system.

In region 162, clustering can be controlled by choice of voltage Vd relative to voltage Vc. If $Vd = Vc$, there is no potential difference between ring 172 and screen 100 and no fragmentation can occur between ring 172 and screen 100. Alternatively, voltage Vd can be made sufficiently different from voltage Vc so that enough energy is provided to break relatively loose clusters, or if desired, to break apart clusters or ions with higher energy bonds.

In addition, in order to optimize transmission of desired masses through the lens formed by rings 170, 172 during mass scanning, voltages Va, Vb, Vc, Vd can be programmed to vary to maintain optimum transmission as different masses are scanned.

It will be seen that the focussing applied in region 160 is another example of the crossed fluid and electric fields used in the concentration of the product ions prior to their injection into the vacuum chamber, but now the crossed fields are applied in a region of varying fluid density.

We claim:

1. Apparatus for transferring matter or species between a vacuum chamber and a gaseous medium, comprising:
   1. a vacuum chamber having a first inlet orifice therein, said vacuum chamber having an interior surface,
   2. a gas curtain chamber outside said vacuum chamber and having a second inlet orifice therein, said gas curtain chamber also having an outlet orifice connected to said first inlet orifice,
   3. conduit means connected to said second inlet orifice for supplying said gaseous medium, at a first selected pressure, to said second inlet orifice,
   4. supply means for supplying a curtain gas which has a low reactivity with said matter or species and which when deposited in solid phase at a predetermined temperature has a vapour pressure of substantially less than atmospheric pressure, at a second selected pressure greater than said first selected pressure, said supply means being connected to said gas curtain chamber for supplying said curtain gas to said gas curtain chamber at said second selected pressure, so that said curtain gas will flow out of said gas curtain chamber into said conduit means through said second inlet orifice and will also flow into said vacuum chamber through said outlet orifice and said first inlet orifice.
   5. means connected to said vacuum chamber for cooling at least a portion of said interior surface thereof to said predetermined temperature whereby to condense said curtain gas on said portion of said surface, thereby evacuating said vacuum chamber,
   6. and means associated with said conduit means, said gas curtain chamber and said vacuum chamber for moving said matter or species along a path extending through said gaseous medium in said conduit means, through said first inlet orifice and said curtain gas, and through said outlet orifice and said second inlet orifice into said vacuum chamber, whereby said curtain gas serves to block ingress of said gaseous medium into said vacuum chamber while permitting passage of said matter or species between said vacuum chamber and said conduit means, and by its condensation enables maintainance of a vacuum in said chamber.

2. Apparatus according to claim 1 wherein said means for moving includes means for moving said matter or species from said gaseous medium into said vacuum chamber.

3. Apparatus according to claim 1 wherein said vapour pressure at said predetermined temperature is less than $10^{-4}$ torr.

4. Apparatus according to claim 3 and including means located in said conduit means for forming ions in said gaseous medium, said ions constituting said matter or species, said means for moving including means for generating an electric field for moving said ions from said conduit means into said vacuum chamber.

5. Apparatus according to claim 4 wherein said curtain gas is selected from the group consisting of argon, nitrogen, carbon dioxide and a freon gas.

6. Apparatus according to claim 4 wherein said means for moving comprises means for guiding said ions along a pre-determined path in said chamber, said portion of said surface encircling said pre-determined path.

7. Apparatus according to claim 6 and including mass analyzer means within said chamber for receiving and analyzing said ions.

8. A method of transferring matter or species between a vacuum chamber and a gaseous medium, comprising:
   a. supplying said gaseous medium at a selected pressure to a first region,
   b. selecting a curtain gas which, when deposited in solid phase at a predetermined temperature, has a vapour pressure substantially less than atmospheric pressure,
   c. directing said curtain gas into a second region adjacent said first region at a pressure greater than said selected pressure, and thereby preventing said gaseous medium from entering said second region,
   d. directing at least some of said curtain gas from said second region into said vacuum chamber,
   e. cooling at least a portion of the interior surface of said vacuum chamber to below said predetermined temperature, whereby to condense said curtain gas on said portion of said interior surface, thereby evacuating said vacuum chamber,
   e. and moving said matter or species along a path extending from said first region through said second region and through the curtain gas in said second region, and into said vacuum chamber, whereby said curtain gas functions to prevent said gaseous medium from entering said vacuum chamber while permitting movement of said matter or species between said first region and said vacuum chamber, and also by its condensation functions to maintain a vacuum in said vacuum chamber.

9. A method according to claim 8 wherein said vapour pressure at said predetermined temperature is less than $10^{-4}$ torr.

10. A method according to claim 9 wherein said gas is selected from the group consisting of argon, nitrogen, carbon dioxide and a freon gas.

11. A method according to claim 9 wherein said gaseous medium contains a trace material, said method including the steps of forming ions from said trace material in said first region, said ions constituting said matter or species, and generating an electric field for moving said ions from said first region into said vacuum chamber.

12. A method according to claim 11 and including the step of guiding said ions along a predetermined path in said vacuum chamber away from said portion of said surface.

13. A method according to claim 12 including the step of analyzing said ions.

* * * * *